United States Patent [19]

Kolc et al.

[11] Patent Number: 4,530,714
[45] Date of Patent: Jul. 23, 1985

[54] N-ALIPHATIC AND N,N-ALIPHATIC PHOSPHORIC TRIAMIDE UREASE INHIBITORS AND UREASE INHIBITED UREA BASED FERTILIZER COMPOSITIONS

[75] Inventors: Jaroslav F. Kolc, Morristown; Michael D. Swerdloff, Parsippany; Milorad M. Rogic, Whippany, all of N.J.; Larry L. Hendrickson, Camillus; Michael Van Der Puy, Cheetowaga, both of N.Y.

[73] Assignee: Allied Corporation, Morris Township, Morris County, N.J.

[21] Appl. No.: 571,226

[22] Filed: Jan. 16, 1984

Related U.S. Application Data

[63] Continuation-in-part of Ser. No. 475,987, Mar. 16, 1983, abandoned.

[51] Int. Cl.³ .............................................. C05C 9/00
[52] U.S. Cl. .......................................... 71/28; 71/902
[58] Field of Search ............................ 71/11, 27–30, 71/902

[56] References Cited

U.S. PATENT DOCUMENTS

| 4,182,881 | 1/1980 | Bayless et al. | 546/22 |
| 4,222,948 | 9/1980 | Alaimo et al. | 260/397.7 R |
| 4,225,526 | 9/1980 | Alaimo et al. | 260/397.7 R |
| 4,242,325 | 12/1980 | Bayless et al. | 424/218 |

FOREIGN PATENT DOCUMENTS 830800 3/1960 United Kingdom .
1494774 12/1977 United Kingdom .

OTHER PUBLICATIONS

1978, CA, vol. 89, Abst. #89:89455k, Matzel et al.
1979, CA, vol. 90, Abst. #90:21340j, Oertel et al.
1979, CA, vol. 91, Abst. #91:122724p, Matzel et al.
1979, CA, vol. 91, Abst. #91:139619f, Heber et al.
1981, CA, vol. 94, Abst. #94:101951g, Vlek et al.
1981, CA, vol. 94, Abst. #94:139429f, Bayless et al.

Primary Examiner—Ferris H. Lander
Attorney, Agent, or Firm—Richard C. Stewart, II

[57] ABSTRACT

The invention relates to novel urease inhibited fertilizer compositions containing urea and a urease inhibiting amount of one or more phosphoric triamide compounds, and methods and composition for inhibiting the urease catalyzed hydrolysis of urea through use of such compounds.

52 Claims, 2 Drawing Figures

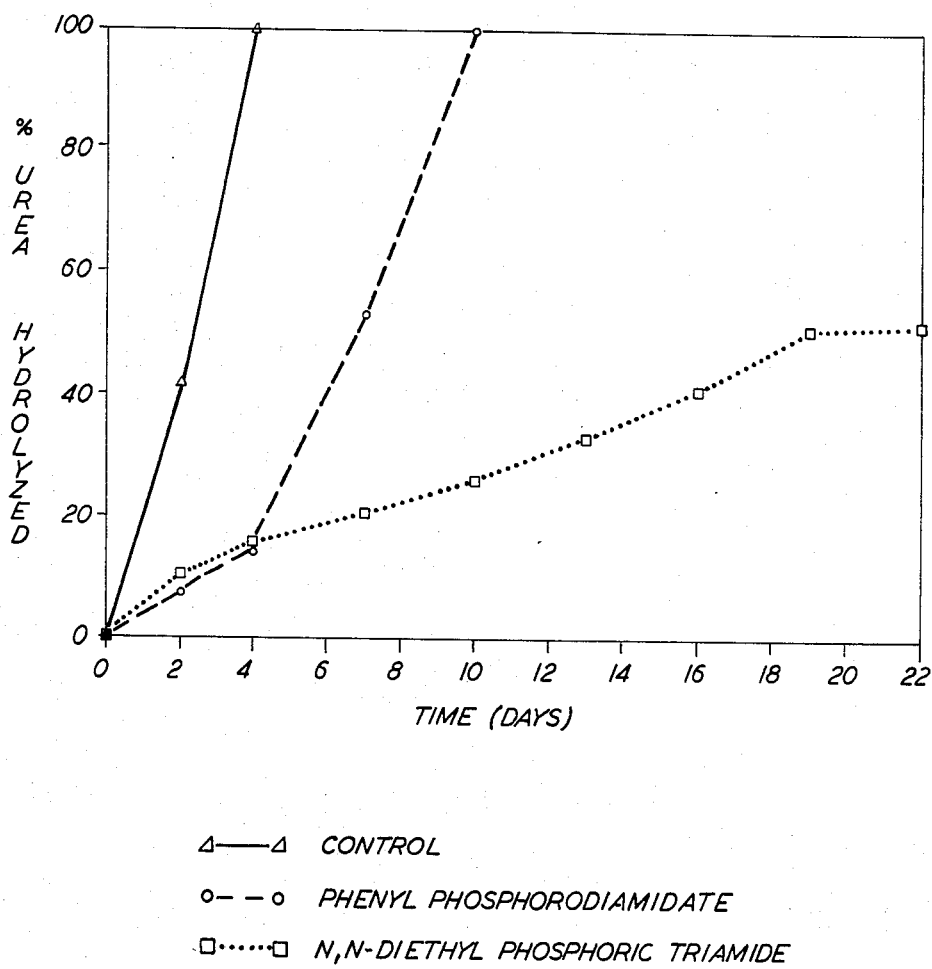

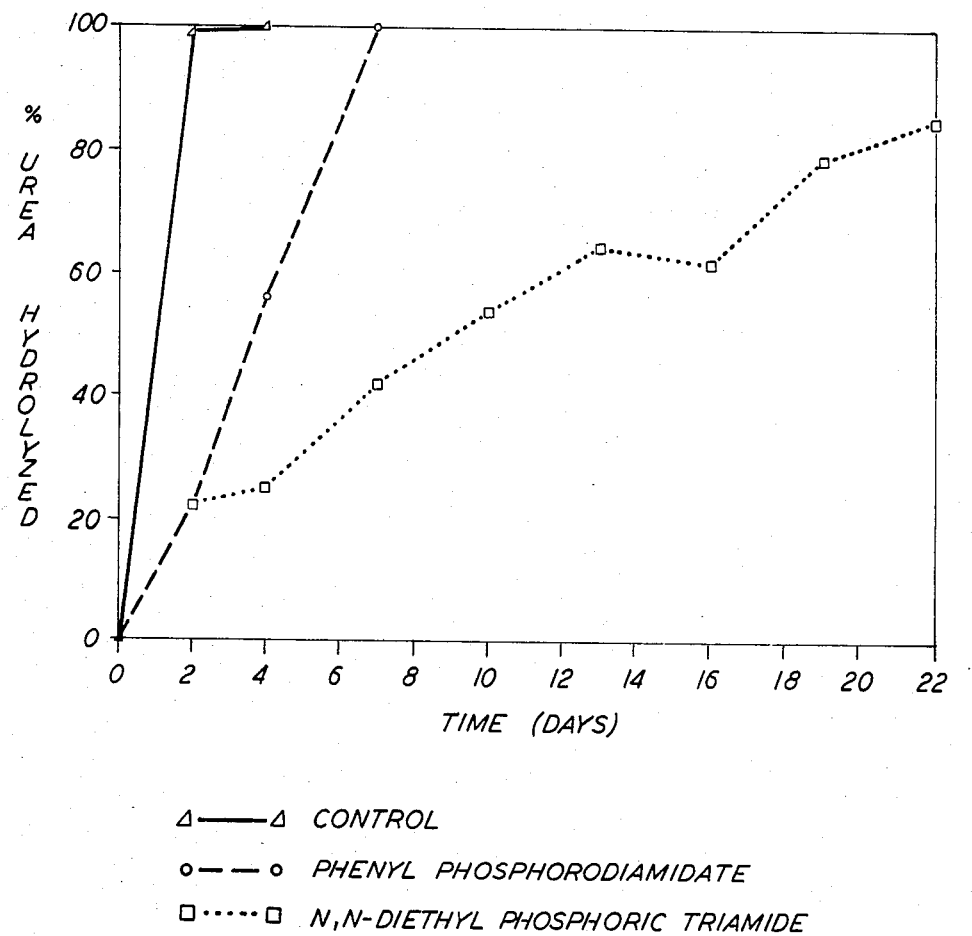

N-ALIPHATIC AND N,N-ALIPHATIC PHOSPHORIC TRIAMIDE UREASE INHIBITORS AND UREASE INHIBITED UREA BASED FERTILIZER COMPOSITIONS

RELATED APPLICATION

This application is a continuation-in-part application of application Ser. No. 475,987 filed Mar. 16, 1983 now abandoned.

BACKGROUND OF THE INVENTION

1. Field of the Invention

This invention relates to novel phosphoric triamide urease inhibitors and to urease inhibited urea based fertilizer compositions. More particularly, this invention relates to urease inhibited urea based fertilizer compositions which contain certain phosphoric triamide compounds as the urease inhibitors, and methods of using such fertilizer compositions to increase plant yield, and compositions and methods of inhibiting the catalytic activity of soil urease by such phosphoric triamide compounds.

2. The Prior Art

It is well known in the art to use urea and urea compositions in fertilizers, for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonia, when urea is placed under or on the surface of soil which contains urease.

Urease, a crystallizable enzyme occurring in numerous bacteria and fungi, as for example *Micrococcus urease*, catalyzes the conversion of urea into ammonia and carbon dioxide. The reactions are as follows:

A portion of the ammonia thus formed is held by absorbing constituents of the soil and is available to plants as nutrient. However, a large amount of the ammonia may be lost to the air. A further problem resulting from the action of urease is that the accumulation of ammonium species in the soil may damage germinating seedlings and young plants.

One approach to the reduction of the problems resulting from the activity of soil urease toward soil applied urea is to find compounds that inhibit urease activity when applied to soils in conjunction with fertilizer urea. This approach has received considerable attention, and several classes of compounds have been used for this purpose.

For example the prior art describes various phosphoro compounds which are useful as urease inhibitors. Illustrative of such prior art are East German Pat. Nos. 142,714; 212,026; 122,177; 122,621 and 130,936, and Great Britain Pat. No. 1,494,774 which patents describe various phosphorotriamides as urease inhibitors. U.S. Pat. No. 4,242,325 describes a method of controlling the enzymatic decomposition of urea to ammonia and carbonic acid due to the action of urease, which method comprises exposing the enzyme to certain phosphoric triamide compounds. U.S. Pat. No. 4,182,881 describes the use of certain N-(diaminophosphinyl)arylcarboxamide compounds as inhibitors of the enzyme urease in the urinary tract. U.S. Pat. No. 4,225,526 describes the use of 8-[(4-aminophenyl)sulfonyl]amino-2-napthalenyl phosphorodiamide as an inhibitor of the enzyme urease, and U.S. Pat. No. 4,222,948 describes the use of ([(4-aminophenyl)sulfonyl]amino)phenyl phosphorodiamide as an inhibitor of the enzyme urease.

Still other prior art describes phosphoric triamide compounds which are useful for other purposes, for example, as flame proofing agents. For example, Great Britain Pat. No. 830,800 describes certain phosphoric triamide compounds which are useful as flame proofing agents.

SUMMARY OF THE INVENTION

In accordance with the present invention, there is provided a unique fertilizer composition comprising urea or a compound which is capable of forming urea when subjected to the use conditions of the composition, and a "urease inhibiting effective amount" of one or more phosphoric triamide compounds of the formula:

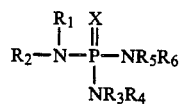

wherein:

X is oxygen or sulfur;

$R_1$ is alkyl, cycloalkenyl, aralkyl, alkenyl, alkynyl, or cycloalkyl;

$R_2$ is $R_1$, hydrogen, or $R_1$ and $R_2$ together may form an alkylene or alkenylene chain which may optionally include one or more heteroatoms of divalent oxygen, nitrogen or sulfur completing a 4, 5, 6, 7, or 8 membered ring system; and $R_3$, $R_4$, $R_5$ and $R_6$ are individually hydrogen or alkyl having 1 to about 4 carbon atoms. In the present specification and claims, the term "phosphoric triamide compounds" is used to refer to these compounds.

Another aspect of this invention relates to a method of enhancing the yield and/or growth of plants by distributing the composition of this invention in the "plant growth medium" in which the plants are being grown within reach of the root system of the plants (hereinafter referred to as "root zone"). As herein, the term "plant growth medium" refers to various natural and artificial medium which support plant growth, including but not limited to soil, potting mixtures of organic and inorganic matter and artificial medium such as polyurethane foam.

Yet another aspect of this invention relates to a method of inhibiting the urease catalyzed hydrolysis of urea applied to some growth medium which comprises distributing a "urease inhibiting effective amount" of one or more of the aforementioned phosphotriamide compounds to the plant growth media prior to, after or in conjunction with the application of urea to said plant growth medium and to a composition for carrying out such method. As used herein, a "urease inhibiting effective amount" is an amount of such phosphoric triamide compounds which when admixed with urea, is capable of inhibiting the urease catalyzed hydrolysis of any urea which may be present in the plant growth medium to any extent.

It has been discovered that by distributing an urease inhibiting effective amount of one or more of the phosphoric triamide compounds in the plant growth media, the activity of urease in the medium is suppressed thereby preventing rapid loss of urea from the media. Furthermore, by proper distribution of the phosphoric triamide compounds in the plant growth medium, the inhibition of the action of urease is effective over a prolonged period of time.

BRIEF DESCRIPTION OF THE DRAWINGS

FIG. 1 is a graph of urea hydrolysis as a function of time for various urease inhibitors at 25° C.

FIG. 2 is a graph of urea hydrolysis as a function of time for various urease inhibitors at 35° C.

DETAILED DESCRIPTION OF THE INVENTION

The application of a urease inhibiting effective amount of one or more of the above-identified phosphoric triamide compounds is essential for the practice of this invention. Preferably, the amount of the phosphoric triamide compound impregnated or distributed in the plant growth media is an amount which is sufficient to inhibit the urease catalyzed hydrolysis of all urea present in the composition. Usually, the plant growth media is impregnated with at least about 0.02 parts of said one or more phosphoric triamide compounds per 1,000,000 parts of the plant growth media. Hereinafter, the abbreviation of "p.p.m" designates parts of one or more phosphoric triamide compounds per million parts of soil or other plant growth media. In the preferred embodiments of this invention, the amount of said phosphoric triamide compounds impregnated in the plant growth media is from about 0.02 to about 5000 p.p.m, and in the particularly preferred embodiments of the invention is from about 1 to about 1000 p.p.m. Amongst these particularly preferred embodiments, most preferred are those embodiments in which the weight percent of said one or more phosphoric triamide compounds is from about 5 to about 100 p.p.m.

Within the aforementioned limitations, the preferred amounts of the one or more phosphoric triamide compounds impregnated or distributed in the growth medium are dependent upon the particular situation. Thus, in determining the amount to be employed, consideration is made not only of the treatment need, i.e., soil pH, temperature, soil type, etc., but also of the mode of application to soil. When the one or more phosphoric triamide compounds are applied in a broadcast application, the amount in p.p.m. is frequently less than in row or band application where, for a substantial depth and width within the vicinity of application, there can be a very high concentration of the one or more phosphoric triamide compounds. When application is made near the root zone of growing plants or when application is made immediately prior to seeding or transplanting, the amounts supplied are frequently at a lower rate than when application is made at the end of the growing season to prepare the soil for the following season. By dispersing very large dosages in the plant growth media, a prolonged inhibition of urease activity can be obtained over a period of many months. The concentration of the one or more phosphoric triamide compounds is eventually reduced to a minimum by decomposition in the soil.

In one method for carrying out the present invention, one or more phosphoric triamide compounds are distributed throughout the plant growth media in a broadcast application, such as by spraying, dusting, distributing in irrigation water, etc. In such application, the one or more phosphoric triamide compounds are supplied in amounts sufficient to permeate the growing area of the plant growth medium with a urease inhibiting effective amount of one or more phosphoric triamide compounds. In field administration, one or more phosphoric triamide compound can be distributed in the plant growth medium in an amount and through such cross-section of the medium as to provide for the presence therein of a urease inhibiting effective amount of the compounds. It is usually preferred that the one or more phosphoric triamide compounds can be distributed to a depth of at least two inches below the soil surface.

In another method for carrying out the present invention, one or more phosphoric triamide compounds are administered to a plant growth medium in a band or row application. In such application, administration is made with or without a carrier in amounts sufficient to supply to the soil or growth medium a urease inhibiting effective amount of the one or more phosphoric triamide compounds. After administration with or without discing or dragging, subsequent irrigation or rainfall distributes the one or more phosphoric triamide compounds throughout the plant growth medium.

In one embodiment of the present invention, the one or more phosphoric triamide compounds are distributed throughout the plant growth medium prior to seeding or transplanting the desired crop plant.

In another embodiment, the soil in the root zone of growing plants is treated with the one or more phosphoric triamide compounds in an amount sufficient to inhibit the action of urease, but sublethal to plant growth. By following such practice, no adverse effect is exerted by the one or more phosphoric triamide compounds upon growth of seeds or plants. Oftentimes, it is desirable to treat the soil or plant growth medium adjacent to plants, and this procedure may be carried out conveniently in side-dressing operations.

In a further embodiment, soil or plant growth medium can be treated with the one or more phosphoric triamide compounds following harvest to prevent rapid loss of urea, and to prevent the build-up of soil urease. Such practice conserves the soil nitrogen for the following growing season. In such application, the upper limit is primarily an economic consideration.

In an additional embodiment, the soil or plant growth medium is treated with a fertilizer composition containing one or more phosphoric triamide compounds in conjunction with urea or one or more urea precursor compounds capable of forming urea in situ on application to the plant growth medium. Urea is a well known, commercially available compound and will not be discussed herein in detail. Illustrative of compounds which are believed to form urea on addition to the soil and are water soluble are formaldehyde condensation products, such as, for example methylolureas, methyleneureas and mixtures thereof. These products and a method for their preparation are described in detail in U.S. Pat. No. 3,462,256. Still other useful sources of urea are water-insoluble urea formaldehyde condensation products such as ureaform. Illustrative of useful water-insoluble urea and formaldehyde condensation products are those whose preparation and use are described in detail in U.S. Pat. Nos. 3,677,736 and 4,033,745.

The amount of urea or urea precursor compound included in the composition of this invention is not critical to the unique advantages thereof, and any amount normally used in conventional urea based fertilizers can be employed. Normally, the amount employed will vary widely depending on a number of factors, including the times and frequency of application. In the preferred embodiments of the invention, the quantity of urea or urea precursor compound may vary from about 0.5 to about 95 weight percent based on the total weight of the composition and in the particularly preferred embodiments may vary from about 1 to about 50 weight percent on the same basis. In the most preferred embodiments of this invention, the quantity of urea or urea precursor compound will vary from about 3 to about 40 weight percent on the aforementioned basis.

The composition on this invention may include other optional ingredients known to those of skill in the art for inclusion in fertilizer compositions. For example, the composition may include sources of potassium, sulfur, phosphorus, boron, zinc, iron, manganese, copper, molybdenum, cobalt and like micronutrients and macronutrients which may be deficient in the soil. The composition may also include plant growth regulators, as for example auxins, cytokinins and the like; pesticides such as insecticides, miticides, herbicides, nematocides and the like; nitrification and urease inhibitors; and non-urea sources of nitrogen.

The composition of this invention can be conveniently prepared according to conventional methods known to those of skill in the art, and therefore such methods will not be described herein in great detail. Briefly stated, the various essential and optional ingredients can be granulated and mixed usually with a carrier and/or diluent, either liquid or solid. Suitable liquid carriers or diluents include water, petroleum distillates or other liquid carriers. Suitable solid carriers or diluents include clay, talc, bentonite, diatomaceous earth, fullers earth and the like.

The fertilizer composition of this invention can be conveniently used in the practice of the method of this invention to increase yields in a wide variety of plants including legume crop plants and cereal crop plants. For example, the required amounts of the fertilizer composition of this invention can be applied to the soil immediately surrounding the plant, i.e., a radius up to about 20 feet, at a rate of application sufficient to obtain the desired increase in plant yield. The rate of application will depend on a number of factors, such as environmental conditions, type of crop plant and the like. The composition is usually applied at a rate of from about 5 to about 600 lbs. of urea nutrient per acre in a total applied aqueous volume of from about 3 to about 1500 gallons per acre. In the preferred embodiments of the method of this invention, the composition is applied at a rate of from about 2 to about 100 pounds of urea per acre in a total applied aqueous volume of from about 6 to about 250 gallons per acre, and in the particularly preferred embodiments at a rate of from about 3 to about 30 pounds per acre in a total volume of from about 9 to about 25 gallons per acre. The composition can be used in the soil or applied to the foliage of the plant, upon the seeds, or the roots of plants without injuring either the foliage, seeds or roots at any time during the growing cycle. Because of the action of the novel urease inhibitors present in the composition, all or a portion of the urease present at the sites of application will be inhibited and greater amounts of urea nutrients will be made available to the plant for longer periods of time.

The method of the present invention can be carried out by distributing the one or more phosphoric triamide compounds in an unmodified form through a plant growth medium. The present method also embraces distribution of one or more such compounds in said medium as a constituent of a liquid or finely divided solid composition. In such practice, the one or more phosphoric triamide compounds can be modified with one or more additaments or soil treating adjuvants including water, petroleum distillates or other liquid carriers, surface-active dispersing agents, inert finely divided solids and fertilizers such as urea or urea precursor compounds capable of forming urea in situ as described above and other fertilizers as, for example, ammonium nitrate and other reduced nitrogen fertilizers. Preferred adjuvants are surface-active dispersing agents, inert finely divided solids, and especially, nitrogen fertilizers; these adjuvants cooperate with the one or more phosphoric triamide compounds so as to facilitate the practice of the present invention and to obtain an improved result. Depending upon the concentration of the one or more phosphoric triamide compounds, augmented compositions can be distributed in the plant growth medium without further modification, or can be considered as concentrates and subsequently diluted with additional inert carrier to produce the ultimate treating composition. The required amount of the phosphoric triamide compounds can be supplied to growth media in effective amounts as for example in from about 1 to about 50 gallons of organic solvent carrier, in from about 5 to about 27,000 or more gallons of aqueous carrier or in from about 20 to about 2000 pounds of solids carrier per acre treated. When an organic solvent carrier is employed, it can be further dispersed in the above volume of aqueous liquid carrier.

The concentration of one or more phosphoric triamide compounds in compositions to be employed for the treatment of growth media is not critical and can vary considerably provided the required dosage of the effective one or more phosphoric triamide compounds is supplied to the plant growth medium. In general, good results are obtained with liquid or solid compositions containing at least about 0.00001 percent by weight of the one or more phosphoric triamide compounds based on the total weight of the composition. In the preferred embodiments of the invention the amount of one or more phosphoric triamide compounds is from about 0.0001 weight percent to about 98 percent and in the particularly preferred embodiments the amount of one or more phosphoric triamide compounds in said composition is from about 0.0001 to about 50 weight percent on the aforementioned basis. Amongst these particularly preferred embodiments most preferred are those embodiments in which the weight percent of one or more phosphoric triamide compounds is from about 0.001 to about 20. Liquid or dust compositions in which the one or more phosphoric triamide compounds are present in higher concentrations can be utilized as such or can be employed as concentrate compositions to be diluted to prepare actual treating compositions.

Liquid compositions containing the desired amount of the one or more phosphoric triamide compounds can be prepared by dispersing the latter in one or more liquid carriers such as water or an organic solvent with or without the aid of a suitable surface active dispersing agent or emulsifying agent. Suitable organic solvents include acetone, diisobutylketone, methanol, ethanol, isopropyl alcohol, diethyl ether, toluene, methylene chloride, chlorobenzene and the petroleum distillates. The preferred organic solvents are those which are of such volatility that they leave little permanent residue in the growth media. Dispersing and emulsifying agents which can be employed in liquid compositions include condensation products of alkylene oxides with phenols and organic acids, alkyl aryl sulfonates, polyoxyalkylene derivatives or sorbitol ester, sugar esters, complex ether alcohols, mahogany soaps and the like. The surface active agents are generally employed in the amount of from 1 to 20 percent by weight of the one or more phosphoric triamide compounds.

Solid compositions containing the active one or more phosphoric triamide compounds can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with one or more solid phosphoric triamide compounds or wet with one or more liquid phosphoric triamide compounds or a solution or dispersion of one or more solid or liquid phosphoric triamide compounds in a volatile organic solvent. Depending upon the proportions of ingredients, these compositions can be employed without further modification or be considered concentrates and subsequently further diluted with a solid surface active dispersing agent, talc, chalk, gypsum or the like to obtain the desired treating composition. Furthermore, such concentrate compositions can be dispersed in water with or without added dispersing agent or agents to prepare aqueous soil treating compositions.

Soil treating compositions can be prepared by dispersing one or more phosphoric triamide compounds in a urea fertilizer. The concentration of one or more phosphoric triamide compounds employed in such compositions should, in general, be sufficient to substantially inhibit the hydrolyses of urea in the fertilizer to ammonia when the fertilizer is distributed in a plant growth medium. The resulting fertilizer composition can be employed as such or can be modified as by dilution with additional nitrogen fertilizer or with an inert solid carrier to obtain a composition containing the desired amount of active agent for treatment of soil. Further, an aqueous dispersion of one or more phosphoric triamide compounds composition can be prepared and administered to the growth medium.

While the composition and method of this invention are particularly suited for agricultural applications for prevention or inhibition of urease catalyzed hydrolysis of urea, they can also be used in other applications where inhibition of the activity of urease is desired. For example, such other applications include use in animal litters, as feed additives, diaper treatment, pharmaceutical applications, urease inhibition in mammalian urinary tracts, and the like. It should be noted that the particular active compound employed in one application may not necessarily be useful in another application. Thus, in the selection of a particular active material for use in an application, such factors as toxicity of the material, the environment in which the material will be used, level of urease inhibition desired and the like must be considered in selecting such material.

The phosphoric triamide compounds which are employed as urease inhibitors in the composition and method of this invention are those of the formula:

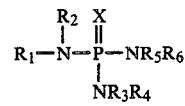

wherein:

X is sulfur or oxygen;

$R_1$ is alkyl, alkenyl, alkynyl, cycloalkyl, aralkyl or cycloalkenyl;

$R_2$ is $R_1$, hydrogen, or $R_1$ and $R_2$ together may form an alkylene or alkenylene chain optionally containing one or more heteroatoms of oxygen, sulfur or nitrogen completing a 3, 4, 5, 6, 7 or 8 membered ring system; and $R_3$, $R_4$, $R_5$ and $R_6$ are the same or different and are individually hydrogen or alkyl having from 1 to about 4 carbon.

Illustrative of permissible $R_1$ substituents are tert-butyl, neopentyl, tetramethylbutyl, methyl, pentyl, hexyl, heptyl, sec-octyl, dodecyl, sec-butyl, ethyl, propyl, oleyl, isopropyl, butyl, propargyl, isobutyl, isopentyl, sec-pentyl, hexyl, sec-heptyl, heptyl, octyl, cyclopropyl, cyclobutyl, propenyl, pentenyl, sec-hexyl, cyclohexyl, hexenyl, cyclopentenyl, allyl, sec-isohexyl, 2-phenylethyl, 2-naphthylethyl, cyclohexenyl, benzyl and the like.

Exemplary of useful $R_2$ substituents are hydrogen, methyl, ethyl, propyl, isopropyl, butyl, isobutyl, pentyl, neopentyl, hexyl, 2-butene, ethylene, 3-butene, 2-propene, acetylene, cyclopropyl, cyclobutyl, cyclopentyl, cyclohexyl, and the like.

Permissible $R_3$, $R_4$, $R_5$ and $R_6$ substituents include hydrogen, methyl, ethyl, propyl, isopropyl, butyl, isobutyl and the like.

The following compounds are illustrative of phosphoric triamide compounds within the purview of the above structural formula which can be prepared simply by selecting appropriate reactants for use in the procedures described below and which can be employed in the practice of this invention.

N-(sec-pentyl)phosphoric triamide
N-(sec-hexyl)phosphoric triamide
N-(sec-isohexyl)phosphoric triamide
N-(n-heptyl)phosphoric triamide
N-(n-propyl)phosphoric triamide
N-(n-butyl)-N-methylphosphoric triamide
N-(sec-butyl)-N-methylphosphoric triamide
N-(sec-pentyl)-N-ethylphosphoric triamide
N-(iso-propyl)-N-methylphosphoric triamide
N,N-diisopropylphosphoric triamide
N-(sec-isohexyl)phosphoric triamide
N-(n-butyl)-N'-methylphosphoric triamide
N-(ethyl)-N'-isopropylphosphoric triamide
N-butyl-N'-ethyl-N''-propylphosphoric triamide
N-3-butenylphosphoric triamide
N-propargylphosphoric triamide
N-neopentylphosphoric triamide
N-hexylphosphoric triamide
N,N-bis-(sec-butyl)phosphoric triamide
N-methyl-N-propylphosphoric triamide
N-(2-cyclohexenylphosphoric triamide
N-cyclopropylphosphoric triamide
N-cyclopentenylphosphoric triamide
N-cyclobutylphosphoric triamide
N-cyclopentylphosphoric triamide
N,N'-dimethyl-N-propylphosphoric triamide N-cyclopentyl-N-benzylphosphoric triamide
N-[2-(1'-naphthyl)ethyl]phosphoric triamide
N-cyclopropyl-N-methylphosphoric triamide
N-ethyl-N-methylphosphoric triamide
N,N-dipropylphosphoric triamide
N-(3-benzylpropyl)phosphoric triamide
N-isobutyl-N-(2-butenyl)phosphoric triamide
N-methyl-N'-benzylphosphoric triamide
N-ethyl-N-(3-phenylpropyl)phosphoric triamide
N-2-(3-pyridyl)ethyl phosphoric triamide
N-(2-thienylethyl)phosphoric triamide
N-(3-phenylpropyl)phosphoric triamide
N-(4-phenylbutyl)phosphoric triamide
N-butyl-N-isopropylphosphoric triamide
N-methyl-N-[2-(1-naphthyl)ethyl]phosphoric triamide
N-diaminophosphinylazolidine
N-diaminophosphinyloxathioazolidine
N-cyclopropylphosphoric triamide
N-(diaminophosphinyl)oxazolidine
N-(2-phenylethyl)phosphoric triamide
N-(diaminophosphinyl)aziridine
N-(diaminophosphinyl)pyrrolidine
N-(diaminophosphinyl)thiazine
N-(2-thienyl)methylphosphoric triamide
N-(diaminophosphinyl)oxathiazine
N-(diaminophosphinyl)oxazine
N-(diaminophosphinyl)triazine
N-(diaminophosphinyl)azine
N-[2-(2'-naphthyl)ethyl]phosphoric triamide
N-5-(1,2,4-thiadiazole)phosphoric triamide
N-5-(3-trichloromethyl-1,2,4-thiadiazole)phosphoric triamide
N-cyclohexyl-N-methylphosphoric triamide
N-methyl-N-propylphosphoric triamide
N-(diaminophosphinyl)morpholine
N-(diaminophosphinyl)thiomorpholine
N-(diaminophosphinyl)piperazine
N-(diaminophosphinyl)pyrimidine
N-methyl-N-(3-phenylpropyl)phosphoric triamide
N-(diaminophosphinyl)pyrrole
N-(diaminophosphinyl)pyrazole
N-(diaminophosphinyl)imidazole
N-(diaminophosphinyl)-1,2,3-triazole
N-(diaminophosphinyl)-1,2,4-triazole
N-(diaminophosphinyl)tetrazole
N-(diaminophosphinyl)indole
N-(diaminophosphinyl)benzotriazole
N-(diaminophosphinyl)benzoimidazole
N-(sec-pentyl)thiophosphoric triamide
N-(sec-hexyl)thiophosphoric triamide
N-(sec-isohexyl)thiophosphoric triamide
N-(n-heptyl)thiophosphoric triamide
N-(n-propyl)thiophosphoric triamide
N-(n-butyl)-N-thiophosphoric triamide
N-(sec-butyl)-N-methylthiophosphoric triamide
N-(sec-pentyl)-N-ethylthiophosphoric triamide
N-(iso-propyl)-N-methylthiophosphoric triamide
N,N-di(n-dodecyl)thiophosphoric triamide
N-(sec-isohexyl)thiophosphoric triamide
N-(n-butyl)-N'-methylthiophosphoric triamide
N-(ethyl)-N'-isopropylthiophosphoric triamide
N-butyl-N'-ethyl-N''-propylthiophosphoric triamide
N-3-butenylthiophosphoric triamide
N-propargylthiophosphoric triamide
N-neopentylthiophosphoric triamide
N-[n-(5-hexynyl)]thiophosphoric triamide
N-octylthiophosphoric triamide
N-methyl-N-propylthiophosphoric triamide N-(2-phenethyl)thiophosphoric triamide
N-(2-cyclohexenyl)thiophosphoric triamide
N-cyclopropylthiophosphoric triamide
N-cyclopentenylthiophosphoric triamide
N-cyclobutylthiophosphoric triamide
N-cyclopentylthiophosphoric triamide
N,N'-dimethyl-N-propylthiophosphoric triamide
N-[2-(1'-naphthyl)ethyl]thiophosphoric triamide
N-cyclopropyl-N-methylthiophosphoric triamide
N-ethyl-N-methylthiophosphoric triamide
N,N-dipropylthiophosphoric triamide
N-(3-benzylpropyl)thiophosphoric triamide
N-isobutyl-N-(2-butenyl)thiophosphoric triamide
N-methyl-N-(1-naphthyl)thiophosphoric triamide
N-ethyl-N-(3-phenylpropyl)thiophosphoric triamide
N-2-(3-pyridyl)ethylthiophosphoric triamide
N-(2-thienylethyl)thiophosphoric triamide
N-(3-phenylpropyl)thiophosphoric triamide
N-(4-phenylbutyl)thiophosphoric triamide
N-isopropylthiophosphoric triamide
N-methyl-N-[2-(1-naphthyl)ethyl]thiophosphoric triamide
N-diaminothiophosphinylazolidine
N-diaminothiophosphinyloxathioazolidine
N-(diaminothiophosphinyl)oxazolidine
N-(2-phenylethyl)thiophosphoric triamide
N-(diaminothiophosphinyl)aziridine
N-(diaminothiophosphinyl)oxathiazolidine
N-(diaminothiophosphinyl)thiazine
N-(2-thienyl)methylthiophosphoric triamide
N-(diaminothiophosphinyl)oxathiazine
N-(diaminothiophosphinyl)oxazine
N,N-dimethylthiophosphoric triamide
N-(diaminothiophosphinyl)triazine
N-(diaminothiophosphinyl)azine
N-[2-(2'-naphthyl)ethyl]thiophosphoric triamide
N-cyclohexyl-N-methylthiophosphoric triamide
N-methyl-N-propylthiophosphoric triamide
N-5-(1,2,4-thiadiazole)thiophosphoric triamide
N-5-(3-trichloromethyl-1,2,4-thiadiazole)thiophosphoric triamide
N-(diaminothiophosphinyl)morpholine
N-(diaminothiophosphinyl)thiomorpholine
N-(diaminothiophosphinyl)piperazine
N-(diaminothiophosphinyl)pyrimidine
N-methyl-N-(3-phenylpropyl)thiophosphoric triamide
N-(diaminothiophosphinyl)pyrrole
N-(diaminothiophosphinyl)pyrazole
N-(diaminothiophosphinyl)imidazole
N-(diaminothiophosphinyl)-1,2,3-triazole
N-(diaminothiophosphinyl)-1,2,4-triazole
N-(diaminothiophosphinyl)tetrazole
N-(diaminothiophosphinyl)indole
N-(diaminothiophosphinyl)benzotriazole
N-(diaminothiophosphinyl)benzoimidazole Preferred for use in the practice of this invention are phosphoric triamide compounds in which:

X is sulfur or oxygen;

$R_1$ is alkyl, aralkyl, alkenyl or cycloalkyl;

$R_2$ is $R_1$, hydrogen or $R_1$ and $R_2$ together may form an alkylene chain completing a 3, 4, 5 or 6 membered ring system; and $R_3$, $R_4$, $R_5$ and $R_6$ are the same or different and are individually hydrogen or methyl.

Particularly preferred for use in this invention are phosphoric triamide compounds in which:

X is oxygen or sulfur;

$R_1$ is branched chain or linear alkyl having from about 1 to about 8 carbon atoms, phenylalkyl wherein the aliphatic moiety includes from 1 to about 4 carbon atoms, cyclobutyl, cyclopropyl, cyclohexyl or cyclopentyl; and $R_2$, $R_3$, $R_4$, $R_5$ and $R_6$ are hydrogen.

Especially effacious compounds for use in the practice of this invention are N-cyclohexylphosphoric triamide, N,N-dimethylphosphoric triamide, N-benzyl-N-methylphosphoric triamide, N-isopropylphosphoric triamide, N,N-diethylphosphoric triamide, N-ethylphosphoric triamide, N-(n-butyl)phosphoric triamide, N-(n-butyl)thiophosphoric triamide, N-(sec-butyl)phosphoric triamide, N-(n-dodecyl)phosphoric triamide, N,N-diethylthiophosphoric triamide, N-cyclohexyl-N-methylphosphoric triamide, N-(n-octyl)phosphoric triamide, N-allylphosphoric triamide, N-(diaminophosphinyl)piperidine, N-benzyl-N-methylthiophosphoric triamide, N-cyclohexylthiophosphoric triamide, N-(n-hexyl)thiophosphoric triamide, N-(diaminothiophosphinyl)pyrrolidine, N-(sec-butyl)thiophosphoric triamide, N,N-diisopropylthiophosphoric triamide, N-(diaminothiophosphinyl)piperidine, and N,N-di-(n-butyl)thiophosphoric triamide.

Useful compounds can be prepared in accordance with the following reaction scheme:

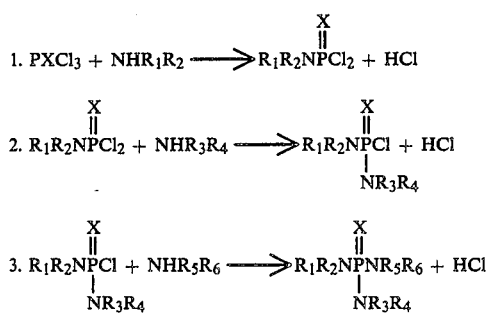

wherein X, $R_1$, $R_2$, $R_3$, $R_4$, $R_5$ and $R_6$ are as described above.

The aforementioned reaction is described in more detail in M. Goehring and K. Niedenzu, Chem. Ber. 89, pp 1768–1771 (1956) and references cited therein and will not be described herein in great detail.

Briefly stated in each step of the three step reaction sequence, substantially equal molar amounts or excesses of the reactants are contacted neat or in an inert solvent with or without a hydrogen chloride acid acceptor. Useful inert reaction solvents include ethyl ether, carbon tetrachloride, methylene chloride, benzene, dioxane, toluene, xylene, tetrahydrofuran, methyl sulfoxide, dimethylformamide, and the like.

The hydrogen chloride acid acceptor employed is a basic material which can be either an inorganic or organic base. Suitable inorganic bases include alkali metal carbonates such as sodium carbonate, potassium carbonate and the like. Organic bases which are useful and preferred for use in the practice of the invention are tertiary amines, as for example pyridine, lutidine, 1,4-diazabicyclo[2.2.2]octane, isoquinoline, trimethylamine, triethylamine, N-ethylpiperidine, quinoline, tributylamine, and the like. Alternatively, an excess of the amine reactant can be used as the acid acceptor.

Reaction temperatures and pressures are not critical. The reaction can be conveniently carried out at a temperature of from about −80° C. to about 200° C., but is preferably carried out at a temperature of from about −30° C. to about 125° C. The reaction can be carried out at sub-atmospheric, atmospheric or super-atmospheric pressure. However, for convenience the reaction is usually carried out at atmospheric or autogeneous pressure.

The order in which the reactants are reacted indicated in the reaction scheme is for illustrative purposes only, and the order of reaction is not critical.

The exact proportions of the reactants are not critical, some of the desired product being obtained when the reactants are employed in any proportions. However, in going to completion, the reaction consumes the reactants and the hydrogen chloride acceptor in substantially equimolar proportions, and the use of the reactants and the hydrogen chloride acceptor in such proportion is preferred, although an excess of the acceptor can be used.

Reaction times are not critical and can be varied widely depending on such factors as the reaction temperature, reactivity of the reactants and the like. The mixture is held within the desired reaction temperature range for a period of time, conveniently from about 10 minutes to 24 hours before cooling. Good yields are usually obtained with reaction times of about 1 to 4 hours.

During the reaction, the hydrochloride salt of the hydrogen chloride acceptor forms and may precipitate from the mixture. This salt can be removed by such conventional procedures as extraction, filtration or centrifugation. The phosphoric triamide product can be separated by such conventional procedures as evaporation and purified by conventional procedures such as distillation and extraction. The product separated as described above may be employed in the control of urease in the soil in accordance with this invention or may be further purified by conventional procedures such as extraction and distillation.

The following specific examples are presented to more particularly illustrate the invention.

EXAMPLE I

Preparation of N,N-Dimethylphosphoric Triamide

Using the procedure described in M. Goehring and K. Niedenzu, Chem. Ber. 89, pp 1768–1771 (1956), 1300–1400 grams of a material containing 53.5% (by weight) of N,N-diethylphosphoric triamide and 46.5% (by weight) of ammonium chloride was prepared by reacting 1035 g of N,N-dimethylphosphoramidic dichloride and ammonia in ether at 0° C. The N,N-dimethylphosphoramidic dichloride was prepared by adding 425 g (9.45 mol) of dimethylamine to 4000 mL (6580 g, 42.7 mol) of phosphorus oxychloride at 0°–10° C., heating the reaction mixture at reflux (105° C.) for 18 h, and distilling the products at reduced pressure ($^{31}$P NMR (CDCl$_3$): δ 17.7 ppm). Pure N,N-dimethylphosphoric triamide can be obtained by extracting the crude material with chloroform, evaporating the chloroform, and recrystallizing the residue from acetone/chloroform. For example, extraction of 130 g of crude material with 1300 mL of hot chloroform provided 30 g of pure material, mp 128.5°–131° C. (lit. 119° C.), after recrystallization $^1$H NMR (DMSO-d$_6$): δ 3.60 (br s, 4H, $\underline{NH_2}$) and 2.60 ppm (d, $J_{H-P}$=11 Hz, 6H, $\underline{CH_3}$).

$^{31}$P NMR (DMSO-d$_6$): δ 19.5 ppm $^{13}$C NMR Proton Decoupled in DMSO-d$_6$): δ 36.9 ppm (d, J$_{C-P}$=2.6 Hz)

Mass Spectrum (70 eV) of sample derivatized with "Methyl-8" reagent (DMF-Dimethylacetal) corresponding to (CH$_3$)$_2$NP(O)[N=CHN(CH$_3$)$_2$]$_2$: m/e 233 (M+), 189 (M+-N(CH$_3$)$_2$), 162 (M+-N=CHN(CH$_3$)$_2$), and 135 (Base, 162+-HCN).

EXAMPLE II

Preparation of N,N-Diethylphosphoric Triamide

Using the procedure described in M. Goehring and K. Niedenzu, Chem. Ber. 89, pp 1768-1771 (1956), 1000 to 1100 g of a material containing 58.5% (by weight) of N,N-diethylphosphoric triamide and 41.5% (by weight) of ammonium chloride was prepared by reacting N,N-diethylphosphoramidic dichloride and ammonia at −30° to −35° C. in ether. The crude N,N-diethylphosphoramidic dichloride was prepared by dropwise addition of 514 mL (366 g, 5.0 mol) of diethylamine in 1000 mL of ether to 459 mL (767 g, 5.0 mol) of phosphorus oxychloride and 404 mL (396 g, 5.0 mol) of pyridine in 900 mL of ether at 0° C. followed by filtration of the precipitated pyridine hydrochloride. Extraction of 57.3 g of crude N,N-diethylphosphoric triamide with 600 mL of hot methylene chloride gave, after evaporation of the methylene chloride, 32.2 g of purified N,N-diethylphosphoric triamide, mp 75°-81.5° C. (lit. 81° C.).

$^1$H NMR (DMSO-d$_6$): δ 3.50 (br s, 4H, NH$_2$), 3.08-2.85 (m, 4H, CH$_2$), and 0.99 ppm (t, J=7 Hz, 6H, CH$_3$).

$^{31}$P NMR (DMSO-d$_6$): δ 18.8 ppm.

$^{13}$C NMR (Proton Decoupled in DMSO-d$_6$): δ 39.06 (d, $^2$J$_{C-P}$=4.5 Hz, CH$_2$) and 14.32 ppm (d, $^3$J$_{C-P}$=2.7 Hz, CH$_3$).

Mass Spectrum (70 eV) of sample derivatized with "Methyl-8" reagent (DMF-Dimethylacetal) corresponding to (CH$_3$CH$_2$)$_2$NP(O)[N=CHN(CH$_3$)$_2$]$_2$: m/e 261 (M+), 217 (M+-N(CH$_3$)$_2$), 190 (M+-N=CHN(CH$_3$)$_2$), 189 (Base), and 162.

Analysis. Calcd. for C$_4$H$_{14}$N$_3$OP: C, 31.78; H, 9.34; N, 27.80; P, 20.49. Found: C, 30.04; H, 9.41; N, 27.19; P, 19.90.

EXAMPLE III

Preparation of N-Allylphosphoric Triamide

N-Allylphosphoric triamide was prepared in accordance with the following modification of the procedure described in L. A. Cates, J. Med. Chem., 13, p. 301-302 (1970). To 19.4 g (0.126 mol) of phosphorus oxychloride in 125 mL of dry ether was added, over a period of 0.5 hours, a solution of 11.5 g (0.20 mol) of allylamine in 25 mL of ether. The resultant solution was stirred for 1 hour at room temperature and filtered. The filtrate was concentrated under vacuum to provide 14.4 g of a clear oil. Distillation could not be performed due to decomposition, but the oil was converted directly into the triamide by adding it to 10 g of ammonia in 150 mL of methylene chloride.

The mixture of product and ammonium chloride was recrystallized with difficulty from ethanol containing a little ether. The NMR spectrum of the recrystallized product (after drying over phosphorus pentoxide) indicated that about 17% by weight of ammonium chloride was still present. The material was submitted for urease tests as described in Example XXIV below without further purification.

EXAMPLE IV

Preparation of N-Benzyl-N-methylphosphoric Triamide

A solution of 16 g (0.13 mol) of benzylmethylamine in 25 mL of ether was added dropwise to a solution of 25 mL (0.27 mol) of phosphorus oxychloride in 200 mL of ether at 0° to 10° C. The resultant solution was stirred ½ hour in an ice bath, and 1 hour at room temperature. The resultant mixture was filtered, and the volatiles were removed from the filtrate under reduced pressure at room temperature to give 19.8 g of crude product containing some phosphorus oxychloride.

$^1$NMR (CDCl$_3$): δ 7.32 (s, 5H), 4.36 (d, 2H, J=12 Hz), and 2.7 ppm (d, 3H, J=16 Hz).

The crude material was added slowly to 15 g of ammonia in 225 mL of methylene chloride at −30° C. After warming to room temperature, the mixture was filtered. The filtrate was evaporated under reduced pressure to give 5 g of a yellow solid (crude product). The yellow solid was extracted with 500 mL of methylene chloride. This extract yielded 2.1 g of an off-white solid (total yield 7.1 g, 55%), which was dried over phosphorus pentoxide. Melting properties were poor, and the solid slowly turned into a gel upon heating, forming a readily flowable liquid at 116°-117° C.

$^1$H NMR (DMSO-d$_6$): δ 7.3 (s, 5H), 4.05 (d, 2H, J=7-8 Hz), 3.6 (br s, 4H), and 2.4 ppm (d, 3H, J=9-10 Hz).

Analysis. Calcd. for C$_8$H$_{14}$N$_3$OP: C, 48.24; H, 7.08; N, 21.10. Found: C, 48.21; H, 7.54; N, 21.12.

EXAMPLE V

Preparation of N-Cyclohexylphosphoric Triamide

Step A: Cyclohexylamine (99.2 g, 1 mol) was dissolved in methylene chloride (50 mL). The solution was cooled to 0° C. and saturated with hydrogen chloride gas. A white, crystalline solid formed which was collected by filtration. The filtrate was resaturated with hydrogen chloride. Both products were combined and dried in vacuum at room temperature. The yield was 91 g (73%).

Step B: Cyclohexylamine hydrochloric from Step A (40.92 g, 0.3 mol) was added to phosphorus oxychloride (230.0 g, 137.3 mL, 1.5 mol); and the resulting mixture was stirred and heated at reflux (105° C.) under nitrogen. The reflux was continued until all of the solid had dissolved and then for an additional 2 hours (total 16 hours). The temperature of the reaction mixture slowly rose as the reaction progressed, and was 114° C. after 16 hours. The reaction mixture was allowed to cool to room temperature and the excess of phosphorus oxychloride was distilled off (25° C., 20 torr). The remaining white, crystalline solid was the desired N-cyclohexylphosphoric triamide, 65 g (100%).

$^1$H NMR (CDCl$_3$): δ 5.04 (br s, 1H, NH), 3.1 (br s, 1H, CH), and 1.0-2.3 ppm (m, 10H, (CH$_2$)$_5$);

IR (KBr): 3160 (NH), 2940 and 2850 (CH$_2$), 1440 (CH$_2$), 1250 (P=O), 570 and 535 cm$^{-1}$ (P—Cl).

Step C: Liquid ammonia (51 g, 3 mol) was dissolved in glyme (200 mL; freshly distilled from sodium) at −78° C. While keeping the solution under a dry ice reflux condenser, a solution of cyclohexylphosphoramidic dichloride in anhydrous glyme (200 mL) was added dropwise to the ammonia solution under nitrogen. A large amount of a white solid was formed as the temperature rose to −40° C. The reaction mixture was stirred vigorously with a mechanical stirred for 1½ hours. The white solid product was filtered off, rinsed with anhydrous ether and dried in vacuum at room temperature. The yield was 84 g (theoretical: 53.1 g of N-cyclohexylphosphoric triamide, 32.0 g of ammonium chloride).

Separation of the final product from ammonium chloride was achieved by repeated extraction with refluxing methylene chloride (4×400 mL). The yield after evaporation of methylene chloride and drying in a vacuum over phosphorus pentoxide and activated charcoal at room temperature was 26.5 g (50%), mp 114°–117° C. Lit.: L. A. Cates, J. Med. Chem. 13, pp 301–2 (1970), mp 113°–116° C.

IR (KBr): 3260 (NH), 2920 and 2840 (CH$_2$), and 1150 cm$^{-1}$ (P=O).

EXAMPLE VI

Preparation of N-(Diaminophosphinyl)piperidine

Piperidine (4.0 mL, 3.4 g, 40 mmol) was dissolved in anhydrous ether (100 mL) and added dropwise to a solution of phosphorus oxychloride (1.83 mL, 20 mmol) in ether (100 mL) maintained at 0° C. under nitrogen. The white precipitate of piperidine hydrochloride was filtered off, and the filtrate was added to a solution of anhydrous ammonia in ether (300 mL) at 0° C. The reaction mixture was stirred for 90 minutes while allowing it to warm up to ambient temperature. The desired N-(diaminophosphinyl)piperidine (1.7 g) was filtered off and dried in a vacuum over phosphorus pentoxide.

EXAMPLE VII

Preparation of N-Isopropylphosphoric Triamide

Isopropylamine hydrochloride (3.8 g, 40 mmol) and phosphorus oxychloride (40 mL, 65 g, 420 mmol) were stirred and refluxed under nitrogen until the reaction mixture became clear (5 hours). Reflux was continued for an additional one hour. After cooling to room temperature, excess phosphorus oxychloride was distilled off under vacuum (T=24°–40° C., p=20–10 torr). The remaining isopropylphosphoramidic dichloride was distilled at 146° C./5 torr to give 4.3 g of white crystals (yield 61%), mp 66°–67° C.

$^1$H NMR (CDCl$_3$): δ 5.0 (br s, 1H, N$\underline{H}$), 3.62 (m, 1H, C$\underline{H}$), and 1.15 ppm (d, 6H, C$\underline{H}_3$);

IR (KBr): 3200 (NH), 2980 (CH$_3$), 1260 (P=O), 570 and 510 cm$^{-1}$ (P—Cl).

Isopropylphosphoramidic dichloride (4.12 g) was dissolved in 60 mL of anhydrous ether and added dropwise to a saturated solution of anhydrous ammonia in 200 mL of anhydrous ether at 0° C. The resulting white precipitate was a mixture of N-isopropylphosphoric triamide (72%) and ammonium chloride (28%), which weighed 5.5 g after drying under vacuum. The pure N-isopropylphosphoric triamide was obtained by extraction with methylene chloride as a semisolid material.

$^1$H NMR (CDCl$_3$): δ 2.6–4.4 (br s, 5H, N$\underline{H}$), 1.9 (m, 1H, C$\underline{H}$), and 1.15 ppm (d, 6H, C$\underline{H}_3$);

IR (neat): 3350 and 3250 (NH), 2960 (CH$_3$), 1380 and 1365 (isopropyl), and 1150 cm$^{-1}$ (P=O).

EXAMPLE VIII

Preparation of N-(n-Butyl)phosphoric Triamide

Using the procedure described in M. Goehring and K. Niedenzu, Chem. Ber. 89, pp 1768–1771 (1956), 127 g of material containing 58.5% (by weight) of N-(n-butyl)phosphoric triamide and 41.5% (by weight) of ammonium chloride was prepared by reacting 100 g of N-(n-butyl)phosphoramidic dichloride and ammonia in ether at −30° to −35° C. The N-(n-butyl)phosphoramidic dichloride was obtained from the distillation (130° C., 0.075 torr) of the mixture prepared by reacting 65 g (0.60 mol) of n-butylamine hydrochloride and 275 mL (459 g, 3.0 mol) of phosphorus oxychloride (5 h of heating at 125°–135° C.). Extraction of crude N-(n-butyl)phosphoric triamide with hot chloroform followed by recrystallization in carbon tetrachloride/chloroform at −10° C. gave purified N-(n-butyl)phosphoric triamide.

$^1$H NMR (CDCl$_3$): δ 8.0–6.0 and 4.4–3.8 (br s, N$\underline{H}$), 2.95 (br m, NH$_2$ and C$\underline{H}_2$), 1.40 (br, C$\underline{H}_2$), and 0.90 ppm (br m, C$\underline{H}_3$).

Mass Spectrum (70 eV) of sample derivatized with "Methyl-8" reagent (DMF-Dimethylacetal) corresponding to CH$_3$CH$_2$CH$_2$CH$_2$NHP(O)[N=CHN(CH$_3$)$_2$]: m/e 261 (M$^+$), 219 (M$^+$-CH$_2$CH$_2$CH$_3$), and 189 (M$^+$-CH$_3$CH$_2$CH$_2$CH$_2$NH).

Analysis: Calcd. for C$_4$H$_{14}$N$_3$OP: C, 31.78; H, 9.34; N, 27.80; P, 20.49. Found: C, 31.63; H, 9.25; N, 26.55; P, 19.07.

EXAMPLE IX

Preparation of N-(n-Butyl)thiophosphoric Triamide

Using the procedure described in M. Goehring and K. Niedenzu, Chem. Ber. 89, pp 1768–1771 (1956), 30 g (68%) of pure N-(n-butyl)thiophosphoric triamide was prepared by reacting 51 g of n-butylthiophosphoramidic dichloride and ammonia in ether at −30° to −35° C. The product was soluble in ether, and was obtained free from ammonium chloride by-product by simple evaporation of the ether filtrate. The n-butylthiophosphoramidic dichloride was obtained from the distillation (105° to 112° C., 0.75 torr) of the mixture resulting from the reaction of 37.7 g (0.30 mol) of n-butylamine hydrochloride and 152 mL (1.5 mol, 254 g) of thiophosphoryl chloride (72 h at 135° C.) and had the following NMR spectrum.

$^1$H NMR(CDCl$_3$): δ 4.8–3.8 ppm (br s, 1H, N$\underline{H}$), 3.25 (m, 2H, C$\underline{H}_2$NH—), 1.60 (m, 4H, C$\underline{H}_2$), and 0.97 ppm (br t, 3H, C$\underline{H}_3$).

The N-(n-Butyl)thiophosphoric triamide prepared in this manner had the same melting point (54° C.) as reported by Goehring and Niedenzu.

$^1$H NMR (CDCl$_3$): δ 4.2–2.0 (br m, 5H, NH and CH$_2$), 1.42 (m, 4H, C$\underline{H}_2$), and 0.89 ppm (br t, 3H, C$\underline{H}_3$).

$^1$H NMR (D$_2$O): δ 2.95 (m, 2H, C$\underline{H}_2$NH—), 1.42 m, 4H, C$\underline{H}_2$), and 0.90 ppm (br t, 3H, C$\underline{H}_3$).

$^{31}$P NMR (DMSO-d$_6$): δ 59.72 ppm $^{13}$C NMR (Proton Decoupled in DMSO-d$_6$): δ 41.75 (d, $^2J_{C-P}$=2.2 Hz, 1C, C$\underline{H}_2$NH—), 33.70 (d, $^3J_{C-P}$=7.9 Hz, 1C, C$\underline{H}_2$CH$_2$NH—), 19.98 (s, 1C, CH$_3$C$\underline{H}_2$—), and 13.78 ppm (s, 1C, C$\underline{H}_3$).

Mass Spectrum (70 eV) of sample derivatized with "Methyl-8" reagent (DMF-Dimethylacetal) corresponding to CH$_3$CH$_2$CH$_2$CH$_2$NHP(S)[N=CHN(CH$_3$)$_2$]$_2$: m/e 277 (M$^+$), 206 (M$^+$-(N=CHN(CH$_3$)$_2$), and 173 (Base, M$^+$-SNH(CH$_2$)$_3$CH$_3$).

EXAMPLE X

Preparation of N,N-Diethylthiophosphoric Triamide

Using the procedure described in M. Goehring and K. Niedenzu, Chem. Ber. 89, pp 1768–1771 (1956), 37 g of crude N,N-diethylthiophosphoric triamide containing ammonium chloride as a by-product was prepared by reacting N,N-diethylthiophosphoramidic dichloride and ammonia in ether at −30° C. The crude N,N-diethylthiophosphoramidic dichloride used was obtained by filtration of the reaction mixture resulting from the addition of 31.9 g (0.30 mol) of diethylamine to 30.5 mL (50.8 g, 0.30 mol) of thiophosphoryl chloride and 24.2 mL (23.2 g, 0.30 mol) of pyridine in 200 mL of ether at 0° C. The N,N-diethylthiophosphoramidic dichloride had the following NMR spectra.

$^1$H NMR (CDCl$_3$): δ 3.70 and 3.40 (q, J=7 Hz, 2H each, C$\underline{H}_2$) and 1.25 ppm (t, J=7 Hz, 6H, C$\underline{H}_3$.

$^{31}$P $\overline{\text{N}}$MR (CDCl$_3$): δ 61.3 ppm.

$^{13}$C NMR (Proton Decoupled in CDCL$_3$): δ 42.32 (d, $^2$J$_{C-P}$=3.7 Hz, 2C, C$\underline{H}_2$) and 13.35 ppm (d, $^3$J$_{C-P}$=3.5 Hz, 2C, C$\underline{H}_3$).

Extraction of the crude N,N-diethylthiophosphoric triamide with 500 mL of hot chloroform provided 19.5 g of product as an oily liquid free of ammonium chloride. Recrystallization of a portion of this material from hexane/carbon tetrachloride gave pure N,N-diethylthiophosphoric triamide as yellow crystals, mp 54°–58° C. (lit. 64° C.).

$^1$H NMR (CDCl$_3$): δ 3.6–2.0 (m and br s, 8H, C$\underline{H}_2$ and N$\underline{H}_2$) and 1.20 ppm (t, J=8 Hz, 6H, C$\underline{H}_3$).

$^{31}$P $\overline{\text{N}}$MR (CDCl$_3$): δ 64.00 ppm.

$^{13}$C NMR (Proton Decoupled in CDCL$_3$): δ (d, $^2$J$_{C-P}$=5.0 Hz) and 14.57 ppm (d,$^3$J$_{C-P}$=3.4 Hz).

Mass Spectrum (70 eV of sample derivatized with "Methyl-8" reagent (DMF-Dimethylacetal) corresponding to (CH$_3$CH$_2$)$_2$NP(S)[N=CHN(CH$_3$)$_2$]$_2$: m/e 277 (M+), 206 (M+-N=CHN(CH$_3$)$_2$), 205 (M+-(CH$_3$CH$_2$)$_2$N) and 173 (M+-(CH$_3$CH$_2$)$_2$NS).

EXAMPLE XI

Preparation of N-(n-Octyl)phosphoric Triamide

N-(n-Octyl)phosphoric triamide was prepared using the procedure of M. Goehring and K. Niedenzu, Chem. Ber. pp 1768–1771 (1956), as per L. A. Cates, J. Med. Chem. 13, pp 301–302 (1970). The reaction of 49.7 g (0.300 mol) of n-octylamine hydrochloride with 135 mL (226 g, 1.50 mol) of phosphorus oxychloride at 125° C. for 16 h provided, after distillation at 148°–152° C. (0.5 torr), 66.2 g (90%) of N-(n-octyl)phosphoramidic dichloride.

$^1$H NMR (CDCl$_3$): δ 5.45 (br m, 1H N$\underline{H}$), 3.14 (br m, 2H, C$\underline{H}_2$NH—), 1.35 (br s, 12H, C$\underline{H}_2$), and 0.85 ppm (br t, 3H, C$\underline{H}_3$).

Reaction of the N-(n-octyl)phosphoramidic dichloride with ammonia in ether at −30° C. resulted in 74.5 g (97%) of crude N-(n-octyl)phosphoric triamide contaminated with ammonium chloride. Extraction of this material with 1500 mL of hot chloroform gave 28.6 g (59%) of pure N-(n-octyl)phosphoric triamide, mp 102°–114° C. (lit. 106°–110° C.).

$^1$H NMR (CDCl$_3$): δ 7.6–2.0 (br, N$\underline{H}$), 2.85 (br s, CHNH—), 1.26 (br s, C$\underline{H}_2$), and 0.85 ppm (br t, C$\underline{H}_3$).

Mass Spectrum (70 eV) of sample derivatized with "Methyl-8" reagent (DMF-Dimethylacetal) corresponding to CH$_3$(CH$_2$)$_6$CH$_2$NHP(O)[N—CHN(CH$_3$)$_2$]$_2$: m/e 317 (M+), 274 (M+-C$_3$H$_7$), 260 (M+-C$_4$H$_9$), 246 (M+-C$_5$H$_{11}$ or M+-N=CHN(CH$_3$)$_2$), 190, and 189 (M+-CH$_3$(CH$_2$)$_6$CH$_2$NH).

EXAMPLE XII

Preparation of N-Ethylphosphoric Triamide

A mixture of 65.2 g (0.800 mol) of ethylamine hydrochloride and 220 mL (368 g, 2.40 mol) of phosphorus oxychloride was heated at reflux (115°–120° C.) until the evolution of hydrogen chloride gas ceased. The reaction mixture was cooled, excess phosphorus oxychloride was removed under vacuum, and N-ethylphosphoramidic dichloride was distilled at 85°–100° C. (0.005 torr) as a colorless liquid (122 g, 94%).

$^1$H NMR (CDCl$_3$): δ 6.0–5.2 (br s, 1H, N$\underline{H}$), 3.65–2.80 (m, 2H, C$\underline{H}_2$), and 1.28 ppm (br t, J=7 Hz, 3H, C$\underline{H}_3$).

The dichloride was dissolved in 275 mL of ether and added dropwise over a 2 h period to a solution of 150 mL of liquid ammonia (about 6 mol) in 350 mL of ether at −35° C. After stirring for another hour, the mixture was filtered, washed with ether, and dried in a vacuum at ambient temperature to give 170 g (88%) of white solid containing the product and ammonium chloride. Extraction of 50 g of this material with 500 mL of chloroform yielded 21 g of the desired product as a sticky solid.

$^1$H NMR (DMSO-d$_6$): δ 4.55 (br s, 1H, N$\underline{H}$), 3.75 (br s, 4H, N$\underline{H}_2$), 2.90 (m, 2H, C$\underline{H}_2$), and 1.10 ppm (t, J=7.0 Hz, 3H, C$\underline{H}_3$).

Mass Spectrum (70 eV) of derivative prepared from "Methyl-8" reagent (DMF-Dimethylacetal) showed the M+ at m/e 233 corresponding to CH$_3$CH$_2$NHP(O)[N=CHN(CH$_3$)$_2$]$_2$.

EXAMPLE XIII

Preparation of N-(sec-Butyl)phosphoric Triamide

A mixture of 32.9 g (0.300 mol) of sec-butylamine hydrochloride and 100 mL (184 g, 1.28 mol) of phosphorus oxychloride was heated at reflux (115°–120° C.) for 15 h during which time the evolution of hydrogen chloride gas ceased. The solution was cooled, excess phosphorus oxychloride was removed under vacuum, and N-(sec-butyl)phosphoramidic dichloride was distilled at 90°–106° C. (0.01 torr) as a colorless liquid (53 g, 93%).

The dichloride was dissolved in 200 mL of ether and added dropwise over a 1.5 h period to a solution of 50 mL of ammonia in 500 mL of ether at 35° C. After stirring for another 1 h, the mixture was filtered to give 67.7 (87%) of a sticky, white solid containing the product and ammonium chloride. Extraction of this material with 1000 mL of boiling chloroform followed by evaporation of the chloroform filtrate provided 44.2 g of a clear, viscous oil. The oil was dissolved in 150 mL of hot methylene chloride, the resulting solution was filtered, and the methylene chloride was evaporated to give 40.7 g (90%) of the product as a clear oil that partially solidified upon standing.

$^1$H NMR (CDCl$_3$): δ 3.80 and 3.15 (br m, 6H, N$\underline{H}$, N$\underline{H}_2$, and C$\underline{H}$) and 2.0–0.80 ppm (m, 8H, C$\underline{H}_2$ and C$\underline{H}_3$)

$^{31}$P NMR (CDCl$_3$): δ 16.5 ppm.

$^{13}$C NMR (CDCl$_3$) (Proton Decoupled): δ 48.98 (s, 1C, C$\underline{H}$), 31.94 (d, J$_{C-P}$=6.2 Hz, 1C, C$\underline{H}_2$), 23.10 (d, $^3$J$_{C-P}$=3.9 Hz, 1C, CHC$\underline{H}_3$), and 10.52 ppm (s, 1C, CH$_2$C$\underline{H}_3$).

Mass Spectrum (70 eV) of sample derivatized with "Methyl-8" reagent (DMF-Dimethylacetal) corresponding to CH$_3$CH$_2$CH(CH$_3$)NHP(O)[N=

CH—N(CH$_3$)$_2$]$_2$: m/e 261 (M+), 232 (M+-NHCH(CH$_3$)CH$_2$CH$_3$), and 162 (189+-HCN).

Analysis. Calcd. for C$_4$H$_{14}$NOP: C, 31.78; H, 9.34; N, 27.80; P, 20.49. Found: C, 31.63; H, 9.25; N, 26.55; P, 19.07.

EXAMPLE XIV

Preparation of N-(n-Dodecyl)phosphoric Triamide

Dodecylamine (85 g, 0.46 mol) was dissolved in methylene chloride (500 mL). The solution was cooled to 0° C., and saturated with anhydrous hydrogen chloride (45 minutes). The white, crystalline solid was separated and dried in vacuum over phosphorus pentoxide, to provide 97.5 g (95.5%) of n-dodecylamine hydrochloride.

n-Dodecylamine hydrochloride (44.4 g, 0.2 mol) and phosphorus oxychloride (91.4 mL, 1.0 mol) were reacted under nitrogen. A clear solution formed within 30 minutes, and the evolution of hydrogen chloride was observed. Heating at reflux was continued for 5 hours. Excess phosphorus oxychloride was removed by distillation in vacuum (40 to 5 torr, 24° to 50° C.) forming N-(n-dodecyl)phosphoramidic dichloride as a viscous liquid. The following spectroscopic data were obtained from the liquid:

IR (neat): 3200 (NH); 2925 and 2855 (CH); 1265 cm$^{-1}$ (P=O);

$^1$H NMR (CDCl$_3$): δ 5.0-5.6 (br s, 1H, NH), 2.8-3.3 (br m, 2H, CH$_2$), 1.1-1.7 (br s, 20H, CH$_2$), 0.7-1.0 (br t, 3H, CH$_3$).

The N-(n-dodecyl)phosphoramidic dichloride was dissolved in anhydrous ether (50 mL), and the solution was added dropwise to a stirred, saturated solution of anhydrous ammonia in ether (400 mL) at 0° C. A white precipitate containing the desired N-(n-dodecyl)phosphoric triamide and the by-product ammonium chloride formed, which was isolated by filtration and dried in a vacuum (weight 62.5 g). Pure N-(n-dodecyl)phosphoric triamide was obtained by extracting the white precipitate with refluxing methylene chloride, followed by crystallization from ethanol.

$^1$H NMR (CDCl$_3$): δ 2.7-3.1 (br, 2H, CH$_2$), 1.0-1.6 (br s, 20H, CH$_2$), 0.8-1.0 (br t, 3H, CH$_3$).

EXAMPLE XV

Preparation of N-Cyclohexyl-N-methylphosphoric Triamide

Phosphorus oxychloride (30.7 g, 18.3 mL, 0.20 mol) was dissolved in anhydrous ether (120 mL). The resulting solution was cooled to 0° C., and a solution of N-methyl-N-cyclohexylamine (22.6 g, 26.0 mL, 0.20 mol) and pyridine (15.8 g, 16.2 mL, 0.20 mol) in anhydrous ether (100 mL) was added dropwise under nitrogen over 30 minutes. The reaction mixture was stirred and allowed to warm-up to room temperature (2 hours). The precipitated pyridine hydrochloride was filtered off, and the filtrate was added dropwise to a cooled (0° C.) solution of anhydrous ammonia in ether (500 mL). The resulting white solid (26.0 g, 44% yield) was isolated by filtration, and dried in a vacuum. Part of the solid (consisting of N-cyclohexyl-N-methylphosphoric triamide and ammonium chloride) was extracted with refluxing methylene chloride and the extract was evaporated to dryness to give the product free from ammonium chloride:

$^1$H NMR (DMSO-d$_6$): δ 3.0-4.0 (br, 4H, NH$_2$), 2.45 (d, 3H, CH$_3$), 0.9-1.9 ppm (br m, 11H, cyclohexyl CH$_2$).

IR (KBr): 1200 cm$^{-1}$ (P=O).

EXAMPLE XVI

Preparation of N-Benzyl-N-methylthiophosphoric Triamide

A. N-Benzyl-N-methylthiophosphoramidic Dichloride

A solution of N-benzyl-N-methylamine (2.81 g, 0.32 mol) in 47 mL of ether was added dropwise with stirring to 78.6 g (0.47 mol) of thiophosphoryl chloride in 375 mL of ether at 0° C. under an argon atmosphere. After the addition was complete, the resultant slurry was stirred for 30 min at 0° C., and then for 1 h at 25° C. The amine hydrochloride was removed by filtration and the solvent was concentrated at reduced pressure to provide 28.5 g (92.5%) of a red colored oil.

$^1$H NMR (CDCl$_3$): δ 7.31 (s, 5H), 4.6 (d, 2H, J=15 Hz), 2.82 (d, 3H, J=15 Hz).

No attempt to purify this material was made even though it contained approximately 20% of bis-N-benzyl-N-methylthiophosphoramidic dichloride.

$^1$H NMR (CDCl$_3$): δ 4.30 (d, J=9 Hz) 2.52 ppm (d, J=9 Hz).

B. N-Benzyl-N-methylthiophosphoric Triamide

A solution of 28.5 g (0.133 mol) of N-benzyl-N-methylthiophosphoramidic dichloride in 25 mL of methylene chloride was added dropwise to a solution of 33 mL of anhydrous ammonia (condensed volume) in 275 mL of methylene chloride at −30° C. After the addition was completed, the resultant slurry was allowed to slowly warm to room temperature. The inorganic salts were removed by filtration and the solvent was concentrated at reduced pressure to provide 19.5 g of a red-resinous oil. This oil was triturated with 50 mL of ether and 5 mL of petroleum ether causing an oil to settle from the solution. The solvent was carefully decanted from the oil and the process was repeated five times. The combined organic extracts were concentrated at reduced pressure to provide a yellow solid, mp 40°-43° C.

$^1$H NMR (CDCl$_3$): δ 7.30 (s, 5H), 4.35 (d, 2H, J=9 Hz), 2.8-3.5 (br s, 2.5H), and 2.65 ppm (d, 3H, J=9 Hz); IR (nujol): 3.0 (br), 13.0, 13.5, and 14μ.

The $^1$H NMR data (δ 2.8-3.5 and 2.65 ppm peaks) suggested that this material consisted of approximately 75-80% of the desired compound and 20-25% of the undesired bis-(N-benzyl-N-methyl)thiophosphoric triamide

[$^1$H NMR (CDCl$_3$): δ 2.60 ppm (d, J=9 Hz).].

EXAMPLE XVII

Preparation of N-Cyclohexylthiophosphoric

A. Triamide N-Cyclohexylthiophosphoramidic Dichloride

A solution of 60 mL (0.52 mol) of cyclohexylamine in 180 mL of anhydrous ether was added dropwise to a stirred solution of 264 mL (2.6 mol) of thiophosphoryl chloride in 600 mL of anhydrous ether at −70° C. under an argon atmosphere. After the addition was completed, the resultant slurry was allowed to warm to room temperature and then filtered. The filtrate was concentrated at reduced pressure to provide 42.2 g of a yellow solid, mp 60°-64° C. This material was vacuum distilled at 100°-120° C./0.9 mm (lit. bp 135°-143° C. at 4 mm; Chem. Abstr. 1951, 45, 9080f) to provide a white solid (mp 70°-71° C.) in 23% yield (13.8 g).

¹H NMR (CDCl₃): δ 3.0–4.4 (br s, 2H) and 1.0–2.5 ppm (m, 10H).

B. N-Cyclohexylthiophosphoric Triamide

A solution of N-cyclohexylthiophosphoramidic dichloride (13.8 g, 0.059 mol) in 25 mL of methylene chloride was added dropwise to a solution of 15 mL (condensed volume) of anhydrous ammonia in 125 mL of methylene chloride at −30° C. After the addition was completed, the resultant slurry was allowed to warm to room temperature, filtered, and the solvent was concentrated at reduced pressure to provide 3.4 g (29.8%) of a white solid, mp 148°–150° C.

¹H NMR (DMSO-d)₆ δ 2.55–3.90 (m, 6H) and 0.60–2.1 ppm (m, 10H);

IR (nujol): 2.92 (br), 3.0–3.2 (br), and 13.9μ (P=S).

EXAMPLE XVIII

Preparation of N-(n-Hexyl)thiophosphoric Triamide

A. N-(n-Hexyl)thiophosphoramidic Dichloride

A solution of 30.3 g (0.300 mol) of n-hexylamine and 30.4 g (0.300 mol) of triethylamine in 25 mL of ether was added dropwise to a solution of 127.6 g (0.753 mol) of thiophosphoryl chloride in 375 mL of ether maintained at 15° C. The resulting mixture was stirred for another 75 min at 15° C. and then filtered. The solid was washed with 100 mL of ether and the filtrate was concentrated under vacuum to give 68.7 g of crude dichloride. Distillation at 120°–124° C. (0.35 mm) gave 38.5 g (55%) of pure N-(n-hexyl)thiophosphoramidic dichloride as a clear, colorless liquid.

¹H NMR (CDCL₃): δ 4.0 (br s, 1H) 3.2 (dt, 2H), 1.9–1.1 (m, 8H), and 1.10–0.8 ppm (distorted t, 3H).

IR (neat): 1080 and 720 cm⁻¹ (P=S).

B. N-(n-Hexyl)thiophosphoric Triamide

A solution of 36.0 g (0.154 mole) of N-(n-hexyl)thiophosphoramidic dichloride in 80 mL of methylene chloride was added dropwise to a stirred solution of 40 mL (condensed volume) of anhydrous ammonia in 200 mL of methylene chloride at −30° C. After the addition was completed, the resultant slurry was allowed to slowly warm to room temperature, filtered, and the filtrate was evaporated under reduced pressure to provide 28.5 g (95%) of a white solid, mp 65°–70° C.

¹H NMR(DMSO-d₆): δ 4.70 (br s, 4H), 2.78 (q, 2H), 1.22 (br m, 8H), and 0.80 ppm (br t, 3H);

IR(nujol): 3.0–3.1 (br, N—H) and 14.0μ (P=s).

EXAMPLE XIX

Preparation of N-(Diaminothiophosphinyl)pyrroldidine

A. N-(Dichlorothiophosphinyl)pyrrolidine

A solution of 43.4 mL (0.52 mol) of pyrrolidine in 50 mL of ether was added dropwise to a stirred solution of 116 mL (1.04 mol) of thiophosphoryl chloride in 200 mL of ether at 0° C. (ice bath) under an argon atmosphere. After the addition was completed, the resultant slurry was slowly warmed to room temperature overnight. A trace of pyrrolidinium hydrochloride was removed by filtration and the filtrate was concentrated under vacuum to provide 84.5 g of a clear oil. A portion of this oil (40 g) was distilled at 80° C. (0.25 mm) to provide 18.1 g of the desired dichloride as a clear oil.

¹H NMR (CDCl₃): δ 3.42 (q, 2H) and 2.00 ppm (m, 2H);

IR (neat): 3.4, 13.5 and 14.0μ (P=S)

B. N-(Diaminothiophosphinyl)pyrrolidine

A solution of 18.1 g (0.089 mol) of N-dichlorothiophosphinylpyrrolidine in 50 mL of methylene chloride was added dropwise to a solution of 25 mL (condensed volume) of anhydrous ammonia in 150 mL of methylene chloride at −30° C. After the addition was completed, the resultant slurry was allowed to warm to room temperature. The inorganic salts were removed by filtration, and the solvent was concentrated at reduced pressure to provide 6.3 g (43%) of the desired product as a white solid, mp 95°–99° C.

¹H NMR (DMSO): δ 3.85 (br s, 4H), 3.00 (br q, 4H), 3.00 (bq, 4H), and 3.67 ppm (m, 4H);

IR (nujol): 3.61 (N—H) and 13.5μ (P=S).

EXAMPLE XX

Preparation of N-(sec-Butyl)thiophosphoric Triamide

A. N-(sec-Butyl)thiophosphoramidic Dichloride

A solution of 2-aminobutane (45 mL, 0.449 mol) in 45 mL of anhydrous ether was added dropwise to a solution of 93 mL (0.915 mol) of thiophosphoryl chloride in 200 mL of anhydrous ether at 0° C. under an argon atmosphere. The resultant slurry was stirred while slowly warmed to room temperature. After filtering to remove sec-butylamine hydrochloride (40.6 g), the filtrate was concentrated at reduced pressure to provide 32.3 g (69.7%) of a yellow oil.

¹H NMR (CDCl₃): δ 3.90–4.0 (m, 2H) and 0.7–2.1 ppm (m, 8H).

B. N-(sec-Butyl)thiophosphoric Triamide

A solution 32.3 g (0.157 mol) of N-(sec-butyl)thiophosphoramidic dichloride in 50 mL of methylene chloride was slowly added to a stirred solution of 40 mL (condensed volume) of anhydrous ammonia in 250 mL of methylene chloride under argon at −30° C. After the addition was completed, the resultant slurry was allowed to slowly warm to room temperature overnight. After the inorganic salts were removed by filtration, the solvent was concentrated at reduced pressure to provide 24.2 g (92%) of a white solid, mp 68°–74° C., which was shown to be 72% pure by HPLC (P.E. C-18 reversed phase column, gradient: 60:40 water-methanol to 100% methanol).

¹H NMR DMSO-d₆): δ 4.3 (m) and 1.6–2.1 ppm (m).

IR (nujol): 3.0 (br) and 7.3μ.

EXAMPLE XXI

Preparation of N,N-Diisopropylthiophosphoric Triamide

A. N,N-Diisopropylthiophosphoramidic Dichloride

A solution of diisopropylamine (72 mL, 0.512 mole) in 75 mL of anhydrous ether was added dropwise to a cold (ice bath) solution of 106 mL (1.02 moles) of thiophosphoryl chloride in 300 mL of anhydrous ether under an argon atmosphere. The resultant slurry was allowed to slowly warm to room temperature. After filtering to remove isopropylamine hydrochloride, the filtrate was concentrated under vacuum to provide a red oil (45.2 g, 75.4%).

¹H NMR (CDCl₃): δ 3.1–4.1 (m, 2H) and 1.0–1.7 ppm (m 12H).

B. N,N-Diisopropylthiophosphoric Triamide

A solution of 45.2 g (0.193 mol) of N,N-diisopropylthiophosphoramidic dichloride in 75 mL of methylene chloride was added dropwise to a solution of 48 mL (condensed volume) of anhydrous ammonia in 200 mL of methylene chloride at −30° C. After the addition was completed, the resultant slurry was allowed to slowly warm to room temperature. The inorganic salts were removed by filtration and the filtrate was concentrated at reduced pressure to provide 14.5 g (38%) of a pale yellow solid, mp 93°–98° C.

$^1$H NMR (CDCl$_3$): δ 3.42 (m, 2H) and 0.5–2.0 ppm (m, 16H).

IR (nujol): 3.0 (br), 10.0 (s), 11.5μ (w).

EXAMPLE XXII

Preparation of N-(Diaminothiophosphinyl)piperidine

A. N-(Dichlorothiophosphinyl)piperidine

A solution of 66.3 g (0.67 mole) of piperidine in 100 mL of anhydrous ether was added dropwise to a cold (ice bath) solution of 136.1 mL, (1.34 mol) of thiophosphoryl chloride in 500 mL of anhydrous ether under an argon atmosphere. After the addition was completed, the reaction mixture was stirred for 30 min at 0° C. and then for 48 h at room temperature. After filtering the inorganic salts, the filtrate was concentrated at reduced pressure (25° C. for 30 min and then 40°–50° C. for 1 h) to provide 65.2 g (89.3%) of the dichloride as a colorless oil.

$^1$H NMR(CDCl$_3$): δ 3.0–3.7 (m, 4H) and 1.7 ppm (brs, 6H).

B. N-(Diaminothiophosphinyl)piperidine

A solution of 45.1 g, (0.194 mol) of N-(dichlorothiophosphinyl)piperidine in 100 mL of methylene chloride was added dropwise to a solution of 50 mL (condensed volume) of anhydrous ammonia in 275 mL of methylene chloride at −30° C. The resultant slurry was allowed to slowly warm to room temperature overnight under an argon atmosphere. The inorganic salts were removed by filtration and the filtrate was concentrated under vacuum to provide 17.6 g of a white solid. An additional 7.8 g was obtained by extracting the inorganic material with 300 mL of methylene chloride at room temperature. The combined product (25.4 g, 67.9%) was dried over phosphorus pentoxide for 18 h under vacuum to give the desired product, mp 97°–102° C.

$^1$H NMR (DMSO): δ 3.78 (s, 2H), 2.90 (br, 4H) and 1.42 ppm (s, 5H).

IR (nujol): 3.1 (br) and 7.30μ.

EXAMPLE XXIII

Preparation of N-Di-(n-Butyl)thiophosphoric Triamide

A. N,N-Di-(n-Butyl)thiophosphoramidic Dichloride

A solution of 64.3 g (0.38 mol) thiophosphoryl chloride in 300 mL of ether was cooled in a water bath. To this solution was added over 46 min a mixture of 24.8 g (0.245 mol) of triethylamine and 31.4 g (0.243 mol) of dibutylamine. The temperature of the mixture during the addition was maintained at 20°–23° C. The mixture was stirred for an additional hour and then filtered. Evaporation of the filtrate provided 72 g of a crude oil, which was distilled at 136°–139° C. (1.4 mm) to give 33.0 g (52%) of the dichloride as light yellow liquid.

B. N,N-Di-(n-Butyl)thiophosphoric Triamide

A solution N,N-di-(n-butyl)thiophosphoramidic dichloride (33 g, 0.26 mol) in 40 mL of methylene chloride was added dropwise to a solution 275 mL of methylene chloride containing 313 mL of anhydrous ammonia at −30° C. After the addition was completed, the resultant slurry was allowed to warm to room temperature. The inorganic salts were removed by filtration and the filtrate was concentrated at reduced pressure to provide 25.2 g (89.7%) of the desired product as a clear viscous oil.

$^1$H NMR (DMSO-d$_6$): δ 3.65 (s, 4H), 3.9 (p, 4H), and 0.6–2.8 ppm (m, 14H);

IR (neat): 3.05 (br, NH$_2$), 3.4 (s, C—H), 6.5 (m, P—N) and 6.82μ (m).

EXAMPLE XXIV

Efficacy Test

Efficacy tests were conducted to evaluate the efficacy of certain representative phosphoric triamide compounds as urease inhibitors. The inhibition tests were run in a New York soil (Cazenovia silt loam, pH 7.0 or 7.3) or in a Wisconsin Soil (Plano silt loam, pH 5.3). Evaluations (run in triplicate) consisted of applying 800 micrograms of the test compound in 5 mL of water and 42.8 mg of urea in 1 mL of water to 20 g of air-dry soil in a glass bottle. The bottle was capped with perforated aluminum foil and incubated at 25° C. for three days prior to extraction with 100 mL of a 2M potassium chloride solution containing 0.5 mg of phenylmercuric acetate. The extracts were then analyzed for remaining urea using an autoanalyzer. Percent inhibition was calculated as % Inhibition = [1 − (A − B/A − C)] × 100% where A is urea recovered from unincubated sample (urea added to soil and immediately extracted); B is urea recovered from inhibited sample; and C is urea recovered from the control (uninhibited sample).

The results of these tests are set forth in the following Table I.

TABLE I

| | | % Inhibition | | |
|---|---|---|---|---|
| | | Cazenovian | | Wisconsin |
| No. | Compound | pH 7.0 | 7.3 | pH 5.3 |
| 1 | N,N—Diethylphosphoric Triamide | — | 94 | — |
| 2 | N,N—Dimethylphosphoric Triamide | — | 98 | — |
| 3 | N—Allylphosphoric Triamide | — | 93 | — |
| 4 | N—Benzyl-N—methylphosphoric Triamide | — | 96 | — |
| 5 | N—Cyclohexylphosphoric Triamide | — | 98 | — |
| 6 | N—Diaminophosphinyl-piperidine | — | 94 | — |
| 7 | N—Isopropylphosphoric Triamide | — | 97 | — |
| 8 | N—Ethylphosphoric Triamide | — | 99 | 47 |
| 9 | N—(n-Butyl)phosphoric Triamide | — | 99 | 52 |
| 10 | N—(n-Butyl)thiophosphoric Triamide | — | 98 | 95 |
| 11 | N—(sec-Butyl)phosphoric Triamide | — | 96 | 66 |
| 12 | N—(n-Octyl)phosphoric Triamide | — | 98 | 51 |
| 13 | N—(n-Dodecyl)phosphoric Triamide | — | 81 | 28 |
| 14 | N,N—Diethylthiophosphoric Triamide | — | 61 | 53 |
| 15 | N—Cyclohexyl-N—methylphosphoric | — | 92 | 48 |

TABLE I-continued

| No. | Compound | % Inhibition Cazenovian pH 7.0 7.3 | Wisconsin pH 5.3 |
|---|---|---|---|
| 16* | N—Benzyl-N—methylthiophosphoric Triamide | 43 — | 24 |
| 17* | N—Cyclohexylthiophosphoric Triamide | 84 — | 58 |
| 18* | N—(n-Hexyl)thiophosphoric Triamide | 97 — | 52 |
| 19* | N—(Diaminothiophosphinyl)-pyrrolidine | 77 — | 23 |
| 20* | N—(sec-Butyl)thiophosphoric Triamide | 65 — | 51 |
| 21* | N,N—Diisopropylthiophosphoric Triamide** | No Data — | No Data |
| 22* | N—(Diaminothiophosphinyl)-piperidine | 66 — | 0 |
| 23* | N,N—Di-(n-Butyl)thiophosphoric Triamide | 67 — | 37 |

*These materials were evaluated using only 200 instead of 800 micrograms of compound per 20 g of soil.
**This compound was too insoluble in water to obtain significant data.

EXAMPLE XXV

Several experiments were conducted to demonstrate the long term effectiveness of the phosphoric triamide compounds of this invention as compared to conventional urease inhibitors. FIG. 1 is a plot of percent inhibition versus time in soils at 25° C. for N,N-diethylphosphoric triamide, a urease inhibitor useful in the practice of this invention, and for the known urease inhibitor, phenyl phosphorodiamidate, and FIG. 2 is a plot of percent inhibition versus time in soil at 35° C. for the same compounds. As is apparent from the figures, the duration of the urease inhibiting activity of the composition of this invention is much superior to that of the conventional urease inhibitor.

EXAMPLE XXVI

The superiority of some of the phosphoric triamide compounds used in this invention as long term urease inhibitors as compared to the known urease inhibitor phenyl phosphorodiamidate was further demonstrated by either incubating the inhibited soil (cazenovia) samples at 25° or 35° C. for 11 days or allowing them to volatilize for 11 days prior to urea application. The percent inhibition observed, as determined by the means described in Example XVI except using 200 micrograms of the test compound, are set forth in Table II

TABLE II

| Compound | No Preincubation | % Inhibition Preincubated for 11 days at 25° C. | at 35° C. | Open |
|---|---|---|---|---|
| N—Ethylphosphoric Triamide | 95 | 74 | 55 | 72 |
| N—(n-Butyl)phosphoric Triamide | 96 | 75 | 68 | 78 |
| N—(n-Butyl)thiophosphoric Triamide | 90 | 98 | 89 | 94 |
| N—(sec-Butyl)phosphoric Triamide | 92 | 90 | 85 | 77 |
| N—(n-Octyl)phosphoric Triamide | 95 | 39 | 36 | 66 |
| N—Cyclohexyl-N—methylphosphoric Triamide | 80 | 78 | 78 | 67 |
| Phenyl Phosphorodiamidate | 76 | 26 | 16 | 50 |

What is claimed is:

1. A composition comprising an acceptable carrier and a urease inhibiting effective amount of one or more phosphoric triamide compounds of the formula:

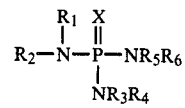

wherein:
X is oxygen or sulfur;
R$_1$ is alkyl, cycloalkenyl, alkenyl, alkynyl, aralkyl or cycloalkyl;
R$_2$ is R$_1$, hydrogen, or R$_1$ and R$_2$ together may form an alkylene or alkenylene chain which may optionally include one or more heteroatoms of oxygen, nitrogen, or sulfur completing a 3, 4, 5, 6, 7 or 8 membered ring structure; and
R$_3$, R$_4$, R$_5$ and R$_6$ are individually hydrogen or alkyl having from 1 to about 4 carbon atoms.

2. A composition according to claim 1 wherein said urease inhibiting amount is at least about 0.00001 weight percent based on the total weight of the composition.

3. A composition according to claim 2 wherein said amount is from about 0.00001 to about 98 weight percent.

4. A composition according to claim 3 wherein said amount is from about 0.0001 to about 50 weight percent.

5. A composition according to claim 4 wherein said amount is from about 0.001 to about 20 weight percent.

6. A composition according to claim 1 wherein X is oxygen.

7. A composition according to claim 1 wherein X is sulfur.

8. A composition according to claim 1 wherein R$_1$ is alkyl, aralkyl, alkenyl, cycloalkyl, or R$_1$ together with R$_2$ form an alkylene chain completing a 3, 4, 5 or 6 membered ring structure.

9. A composition according to claim 8 wherein R$_1$ is alkyl having from 1 to about 8 carbon atoms.

10. A composition according to claim 9 wherein R$_1$ is alkyl having from 1 to about 4 carbon atoms.

11. A composition according to claim 10 wherein R$_1$ is methyl or ethyl.

12. A composition according to claim 8 wherein R$_1$ is cycloalkyl.

13. A composition according to claim 1 wherein R$_1$ is cyclohexyl, cyclopropyl, cyclopentyl or cyclobutyl.

14. A composition according to claim 1 wherein R$_1$ is alkenyl.

15. A composition according to claim 1 wherein R$_1$ is alkenyl having from 2 to about 8 carbon atoms.

16. A composition according to claim 15 wherein R$_1$ is alkenyl having from about 2 to about 4 carbon atoms.

17. A composition according to claim 16 wherein R$_1$ is allyl.

18. A composition according to claim 8 wherein R$_1$ is aralkyl.

19. A composition according to claim 18 wherein R$_1$ is phenylalkyl wherein the aliphatic moiety includes from 1 to about 4 carbon atoms.

20. A composition according to claim 19 wherein R$_1$ is benzyl.

21. A composition according to claim 8 wherein R$_1$ and R$_2$ together form an alkylene chain completing a 3, 4, 5, or 6 membered ring structure.

22. A composition according to claim 21 wherein $R_1$ and $R_2$ together form an alkylene chain completing a 5 or 6 membered ring structure.

23. A composition according to claim 22 wherein $R_1$ and $R_2$ together form an alkylene chain completing a 6 membered ring structure.

24. A composition according to claim 1 wherein $R_3$, $R_4$, $R_5$ and $R_6$ are individudally hydrogen, methyl or ethyl.

25. A composition according to claim 13 wherein $R_3$, $R_4$, $R_5$ and $R_6$ are hydrogen.

26. A composition according to claim 1 wherein $R_2$ is hydrogen or $R_1$.

27. A composition according to claim 26 wherein $R_2$ is hydrogen, alkyl, cycloalkyl, alkenyl or aralkyl.

28. A composition according to claim 27 wherein $R_2$ is alkyl.

29. A composition according to claim 27 wherein $R_2$ is cyclohexyl.

30. A composition according to claim 27 wherein $R_2$ is hydrogen.

31. A composition according to claim 27 wherein $R_2$ is alkyl.

32. A composition according to claim 31 wherein $R_2$ is methyl, ethyl or propyl.

33. A composition according to claim 1 wherein:
X is oxygen or sulfur;
$R_1$ is alkyl, aralkyl, alkenyl or cycloalkyl;
$R_2$ is $R_1$ or hydrogen, or $R_1$ and $R_2$ together form an alkylene chain completing a 3, 4, 5, 6 or 7 membered ring structure; and
$R_3$, $R_4$, $R_5$ and $R_6$ are individually hydrogen, methyl or ethyl.

34. A composition acording to claim 33 wherein:
X is oxygen or sulfur;
$R_1$ is alkyl or alkenyl having from 1 to about 8 carbon atoms, phenylalkyl having from 7 to about 12 carbon atoms, cyclohexyl, cyclopentyl, cyclopropyl or cyclobutyl;
$R_2$ is hydrogen, alkyl or $R_1$ and $R_2$ together form an alkylene chain completing a 5 or 6 membered ring structure; and
$R_3$, $R_4$, $R_5$ and $R_6$ are hydrogen.

35. A composition according to claim 34 wherein X is oxygen.

36. A composition according to claim 34 wherein X is sulfur.

37. A composition according to claim 34 wherein $R_2$ is hydrogen.

38. A composition according to claim 34 wherein $R_1$ is alkyl.

39. A composition according to claim 1 wherein said one or more compounds are selected from the group consisting of N-isopropylphosphoric triamide, N,N-dimethylphosphoric triamide, N-benzyl-N-methylphosphoric triamide, N,N-diethylphosphoric triamide, N-allyphosphoric triamide, N-cyclohexylphosphoric triamide, N-(diaminophosphinyl)piperidine, N-ethylphosphoric triamide, N-(n-butyl)phosphoric triamide, N-(n-butyl)thiophosphoric triamide, N-(sec-butyl)phosphoric triamide, N-(n-octyl)phosphoric triamide, N-(n-dodecyl)phosphoric triamide, N,N-diethylthiophosphoric triamide, N-cyclohexyl-N-methylphosphoric triamide, N-benzyl-N-methylthiophosphoric triamide, N-cyclohexylthiophosphoric triamide, N-(n-hexyl)thiophosphoric triamide, N-(diaminothiophosphinyl)pyrrolidine, N-(sec-butyl)thiophosphoric triamide, N,N-diisopropylthiophosphoric triamide, N-(diaminothiophosphinyl)piperidine, and N,N-di-(n-butyl)thiophosphoric triamide.

40. A method of inhibiting the urease catalyzed hydrolysis of urea at a situs which comprises applying to said situs a urease inhibiting effective amount of one or more phosphoric triamide compounds of the formula:

wherein:
X is sulfur or oxygen;
$R_1$ is alkyl, cycloalkenyl, alkenyl, alkynyl, aralkyl or cycloalkyl;
$R_2$ is hydrogen, $R_1$, or $R_1$ and $R_2$ together may form an alkylene or alkenylene chain which may optionally include one or more heteroatoms of oxygen, nitrogen or sulfur completing a 3, 4, 5, 6, 7 or 8 membered ring structure; and
$R_3$, $R_4$, $R_5$ and $R_6$ are individually hydrogen or alkyl having from 1 to about 4 carbon atoms.

41. A method according to claim 40 wherein said urease inhibiting effective amount of said one or more phosphoric triamide compounds is applied to said situs prior to, after or in conjunction with the application to said situs or urea, and/or one or more urea precursor compounds capable of forming urea in situ on application to said situs.

42. A method according to claim 41 wherein said situs is a plant growth medium.

43. A method according to claim 42 wherein said urease inhibiting effective amount of said phosphoric triamide compounds is applied to said medium prior to the application to said medium of urea and/or said one or more urea precursor compounds.

44. A method according to claim 41 wherein the amount of said one or more phosphoric triamide compounds applied to said plant growth medium is at least about 0.02 p.p.m.

45. A method according to claim 44 wherein said amount is from about 0.02 to about 5000 p.p.m.

46. A method according to claim 45 wherein said amount is from about 1 to about 1000 p.p.m.

47. A method according to claim 46 wherein said amount is from about 5 to about 100 p.p.m.

48. An improved fertilizer composition which comprises urea and/or one or more compounds capable of forming urea under the use conditions of said composition and a urease inhibiting effective amount of one or more phosphoric triamide compounds of the formula:

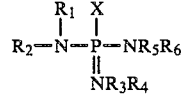

wherein:
X is sulfur and oxygen;
$R_1$ is alkyl, cycloalkenyl, alkenyl, alkynyl, aralkyl or cycloalkyl;
$R_2$ is hydrogen, $R_1$, or $R_1$ and $R_2$ together may form an alkylene or alkenylene chain which may optionally include one or more heteroatoms of oxygen, nitrogen, or sulfur completing a 3, 4, 5, 6, 7 or 8 membered ring structure; and $R_3$, $R_4$, $R_5$ and $R_6$ are individually hydrogen or alkyl having from 1 to about 4 carbon atoms.

49. A method of enhancing plant growth and crop yield which comprises applying the composition according to claim 48 to a plant growth medium within the root zone of said plant.

50. A composition according to claim 1 wherein said carrier is a liquid.

51. A composition according to claim 50 wherein said liquid carrier is selected from the group consisting of water and organic liquids.

52. A composition according to claim 1 wherein said carrier is a finely divided inert solid.

* * * * *